(12) United States Patent
Bauer et al.

(10) Patent No.: US 9,079,122 B2
(45) Date of Patent: Jul. 14, 2015

(54) DISTILLATION COLUMN AND METHOD FOR DISTILLING ACRYLIC ACID

(75) Inventors: Jochen Bauer, Frankfurt (DE); Frank Castillo-Welter, Friedrichsdorf (DE); Markus Kreich, Otzberg (DE); Klaus Kirsten, Mainz (DE); Christoph Steden, Oberursel (DE); Dominic Walter, Darmstadt (DE)

(73) Assignee: Lurgi GmbH, Frankfurt am Main (DE)

( * ) Notice: Subject to any disclaimer, the term of this patent is extended or adjusted under 35 U.S.C. 154(b) by 0 days.

(21) Appl. No.: 13/881,825

(22) PCT Filed: Dec. 9, 2011

(86) PCT No.: PCT/EP2011/006199
§ 371 (c)(1),
(2), (4) Date: May 20, 2013

(87) PCT Pub. No.: WO2012/119629
PCT Pub. Date: Sep. 13, 2012

(65) Prior Publication Data
US 2014/0061025 A1    Mar. 6, 2014

(30) Foreign Application Priority Data
Mar. 10, 2011    (DE) .......................... 10 2011 013 561

(51) Int. Cl.
*B01D 3/22* (2006.01)
*B01D 3/32* (2006.01)
*C07C 51/44* (2006.01)

(52) U.S. Cl.
CPC ....... *B01D 3/32* (2013.01); *B01D 3/322* (2013.01); *C07C 51/44* (2013.01)

(58) Field of Classification Search
CPC .......... B01D 3/32; B01D 3/322; C07C 51/44; C07C 57/04
USPC ............... 203/39, 47; 202/153, 158, 162, 262
See application file for complete search history.

(56) References Cited

U.S. PATENT DOCUMENTS 3,766,021 A * 10/1973 Randall ........................... 203/39
3,873,275 A    3/1975 Bennett
6,679,939 B1 * 1/2004 Thiel et al. ....................... 95/210
2006/0249365 A1 11/2006 Yada et al.

FOREIGN PATENT DOCUMENTS

DE    196 31 332 A1    11/1997
EP    1 095 685 B1    3/2007

OTHER PUBLICATIONS

International Search Report Dated Mar. 27, 2012, Mailed Apr. 5, 2012.
English Translation of International Search Report Dated Mar. 27, 2012, Mailed Apr. 5, 2012.

* cited by examiner

*Primary Examiner* — Nina Bhat
*Assistant Examiner* — Brandi M Doyle
(74) *Attorney, Agent, or Firm* — Norris McLaughlin & Marcus PA

(57) ABSTRACT

A distillation column with external circulation evaporator and a sedimentation zone in the bottom of the column, from which the evaporator circulation is fed, and use of the distillation column for the distillation of acrylic acid.

3 Claims, 3 Drawing Sheets

DISTILLATION COLUMN AND METHOD FOR DISTILLING ACRYLIC ACID

BACKGROUND OF THE INVENTION

This is a 371 of PCT/EP2011/006199 filed 9 Dec. 2011 (international filing date), and claiming priority of German Application 10 2011 013 561.8, filed Mar. 10, 2011

FIELD OF THE INVENTION

This invention relates to a distillation column with external circulation evaporator, which is in particular suitable for carrying out distillation processes in which solid or gel-like constituents are present in the bottom of the column. This invention also relates to a process for the distillation of acrylic acid by using a distillation column according to the invention.

The term distillation column subsequently will be used as generic term which also includes the term rectification column as well as single-stage processes for separation by evaporation, such as the so-called flash distillation.

Distillation columns with external circulation evaporator are known; they are described in principle e.g. in the book: Technische Chemie, 2006 Wiley-VCH Verlag GmbH & Co KGaA, page 338, FIG. 9.55. In the cases described therein, the suction line of the evaporator circulation extends from the deepest point of the bottom space and the part of the bottom product which is provided for further treatment outside the column is withdrawn from the evaporator circulation.

From EP 1 095 685 B1 it is also known that it is possible to install one separate outlet each for the part of the bottom product to be discharged and for the part of the bottom product circulating via the circulation evaporator at the floor of the column bottom. However, both variants have the disadvantage that in distillation processes in which solid or gel-like constituents whose density lies above that of the bottom product are present in the bottom product, the same sink to the floor of the bottom, get into the evaporator circulation and thereby can lead to malfunctions due to soiling, in particular of heat exchanger surfaces.

From EP 1 095 685 B1 it is known that by adding chemical agents it can be attempted to prevent the formation of solid particles in the bottom product. Beside the costs for the chemical additive it is, however, disadvantageous that the quality of the bottom product thereby is changed inadvertently.

As an alternative method, EP 1 095 685 B1 proposes to limit the retention time of the bottom product in the bottom of the column and hence prevent the formation of solid constituents, e.g. due to polymerization, by maintaining certain geometrical dimensions in the floor drain region of the distillation column. In this method it is disadvantageous that merely the formation of solid particles in the bottom of the column is influenced, but a formation of particles in the upper part of the column or the introduction of particles already formed before the column cannot be prevented.

Therefore, it has been the object to provide a distillation column with external circulation evaporator, which without requiring an increased cleaning effort can also be used for distillation processes in which solid and/or gel-like particles are present in the bottom product.

SUMMARY OF THE INVENTION

This object substantially has been solved with the entirety of the features of claim 1 in that in the bottom of the column a sedimentation zone was installed, from whose upper region clarified from solid and/or gel particles or liquid droplets the part of the bottom product provided for the evaporator circulation is withdrawn and the part of the bottom product provided for further treatment outside the column is withdrawn at the deepest point of the bottom of the column. Sedimentation zones are known e.g. from the construction of crystallization evaporators as they are described e.g. in the document U.S. Pat. No. 3,873,275.

In addition, this invention comprises the use of the distillation column according to the invention for the distillation of acrylic acid, in which raw acrylic acid, which still contains undesired amounts of acrylic acid oligomers, is obtained at the top of the column as pure acrylic acid free from oligomers. A particularly advantageous aspect of the distillation column for this use provides that a distillation column according to claim 1 is used, wherein the evaporator circulation (5') is 20 to 200, preferably 40 to 120 $m^3/(h*m^2)$ and the size of the stream (12") withdrawn from the bottom for further treatment is 0.1 to 5, preferably 0.2 to 3 $m^3/(h*m^2)$, each based on the inner cross-sectional area of the column, wherein the ratio of the diameter of the column (1") and of the bottom (2") is 1:0.1 to 0.9, preferably 1:0.15 to 0.6, and wherein the upwardly directed flow velocity in the sedimentation zone (3") is 0.05 to 1, preferably 0.1 to 0.6 m/s. The objective of the invention to obtain a rather small amount of precipitated solid or gel particles in the evaporator circulation is achieved best when said parameters are maintained. This is true in particular when the distillation column according to the invention is used for the distillation of acrylic acid; in this separation operation in particular particles of acrylic acid polymer are obtained in the bottom of the column. When designing the distillation column within the parameter ranges taught in claim 1, a good particle separation is achieved and at the same time a high separation efficiency with regard to the pure acrylic acid. Other designs of the distillation column outside the features of claim 3 provide less satisfactory separation results with regard to the particle separation. Retracting the bottom of the column, i.e. designing the bottom of the column with a smaller diameter than the column, has proven quite effective in the distillation of acrylic acid, as this provides for a more accurate measurement of the amount of liquid present in the bottom.

Further developments, advantages and possible applications of the invention can also be taken from the following description of embodiments and the drawings. All features described and/or illustrated form the invention per se or in any combination, independent of their inclusion in the claims or their back-reference.

BRIEF DESCRIPTION OF THE DRAWINGS

With reference to the drawing, FIGS. 1 and 2, a distillation column according to the invention will each be described by way of example. FIG. 3 shows the lower part of a distillation column with retracted bottom, as it is commonly used for acrylic acid distillation.

DETAILED DESCRIPTION

The distillation column (A, A', A") substantially consists of the column (1, 1', 1") and the column bottom (2, 2', 2"). The column bottom is equipped with the sedimentation zone (3, 3', 3"). The design of the sedimentation zone depends on the parameters of the respective process for which the column is used. The size of the mass flows, the material properties of the substances present and the space conditions present at the site of erection of the column will have to be considered.

Figure 1:
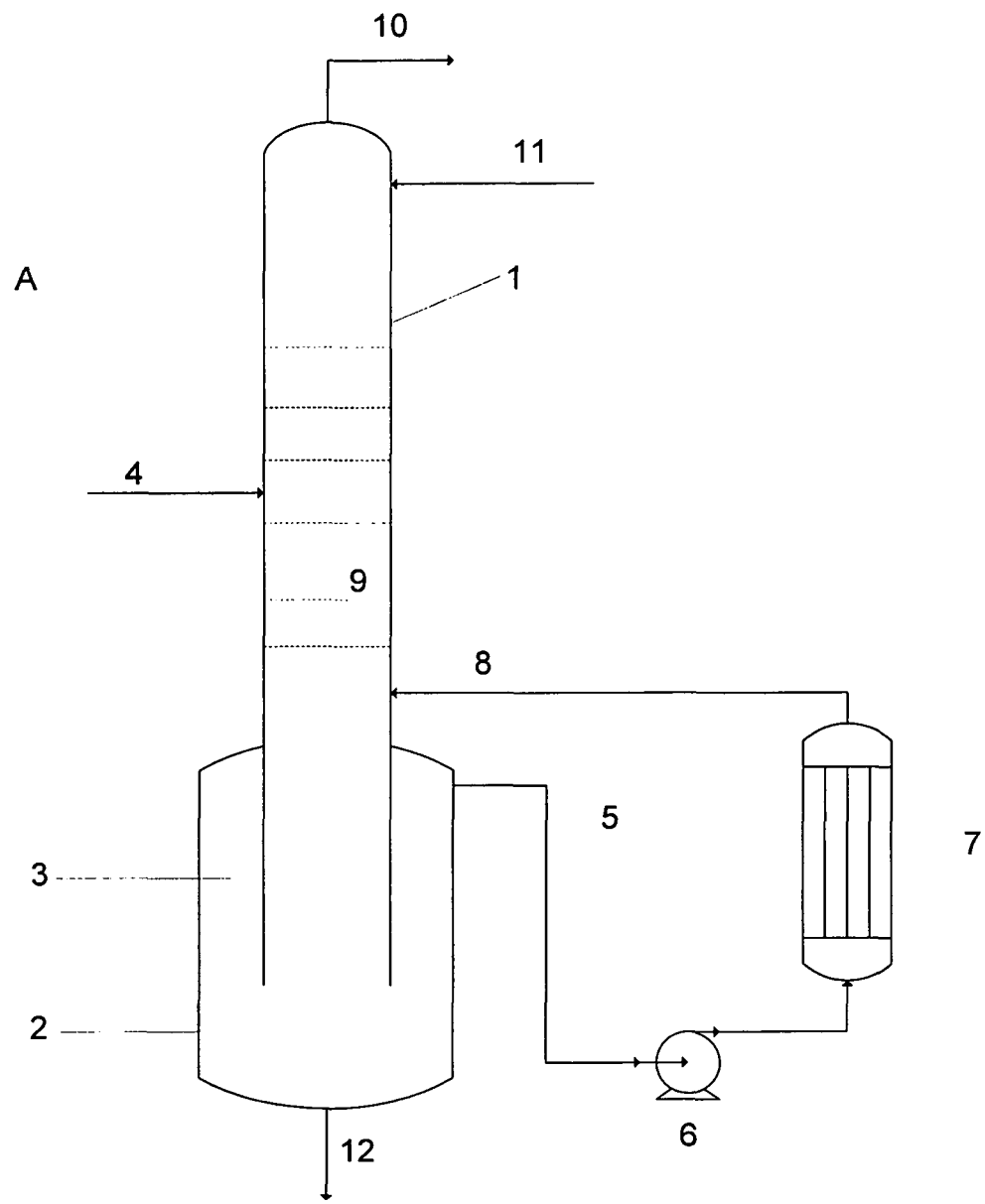
FIG. 1 illustrates a sedimentation zone protruding beyond the cross-section of the column.

FIG. 1 shows a sedimentation zone protruding beyond the cross-section of the column. This construction is to be preferred when the sedimentation of the particles in the bottom product only takes place slowly and therefore a great retention time is required in the sedimentation zone.

Figure 2:
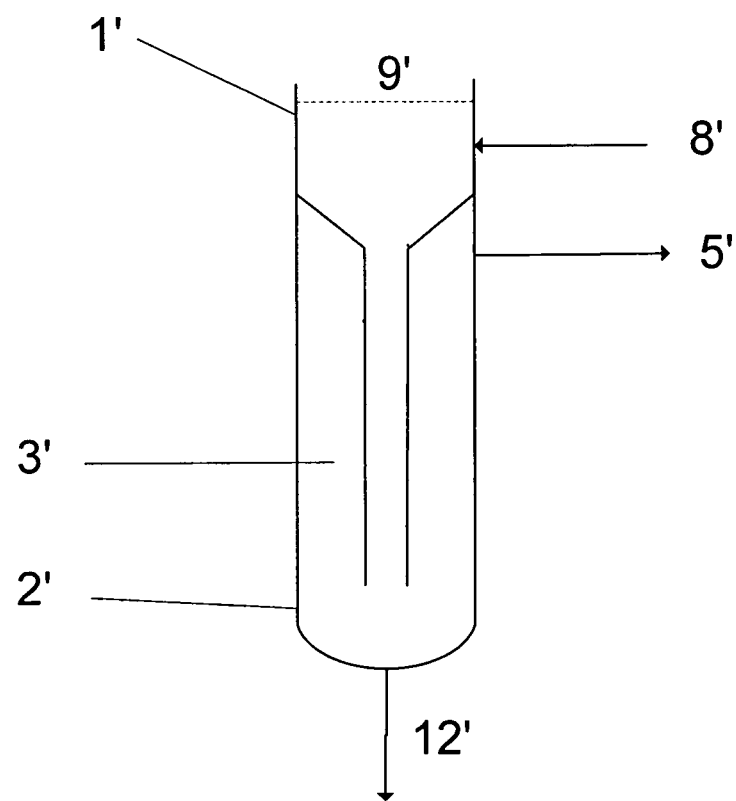
FIG. 2 illustrates an embodiment in which the sedimentation zone is placed in the cross-section of the column.

FIG. 2 shows an embodiment in which the sedimentation zone is placed in the cross-section of the column. This construction is to be preferred when the space conditions are confined and such great retention times are not required in the sedimentation zone.

Via the conduit (4) the mixture to be separated is charged into the column. Via the conduit (5, 5', 5") bottom product is withdrawn from the upper part of the sedimentation zone (3, 3', 3") into the evaporator circuit, conveyed through the evaporator (7) by the pump (6), and conveyed back into the column (1, 1', 1") via the conduit (8, 8', 8") below the exchange trays (9, 9'). Via the conduit (10) the distillate leaves the column (1), via the conduit (11) the return flow of the condensed distillate is recirculated from the non-illustrated external condenser. Bottom product loaded with solid particles is withdrawn at the floor of the column bottom via conduit (12, 12', 12") for further treatment.

Figure 3:
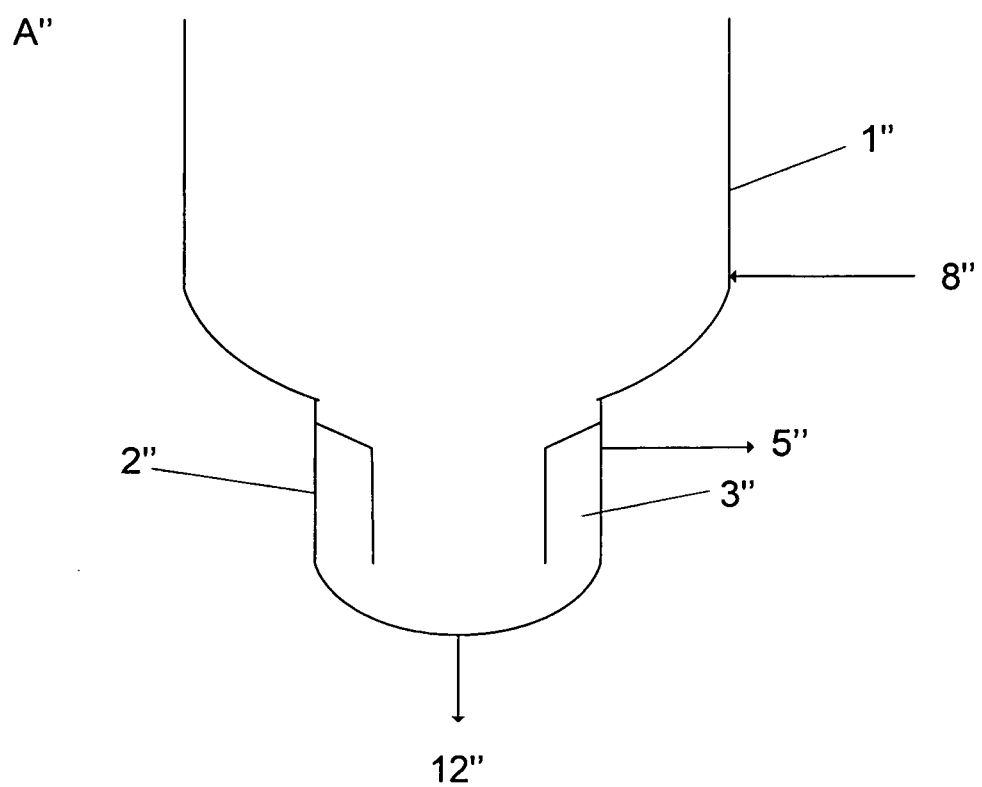
FIG. 3 illustrates an exemplary embodiment of the distillation column according to the invention as it is commonly used for the distillation of acrylic acid.

FIG. 3 shows an exemplary embodiment of the distillation column according to the invention as it is commonly used for the distillation of acrylic acid. Here, the bottom (2") is retracted, i.e. the bottom (2") is designed with a smaller diameter than the column (1"). As a result, fluctuations of the volume of the amount of liquid present in the bottom lead to greater and hence more easily measurable changes of the filling level. Via conduit (5") bottom product clarified from oligomers is withdrawn from the sedimentation zone (3") to the non-illustrated circulation evaporator and again fed into the distillation column (A") via conduit (8"). Via conduit (12") bottom product loaded with oligomers is withdrawn from the distillation column (A") and supplied to the further treatment.

REFERENCE NUMERALS (1, 1', 1") column
(2, 2', 2") bottom
(3, 3', 3") sedimentation zone
(4) educt supply
(5, 5', 5") discharge conduit bottom product to the evaporator circuit
(6) pump
(7) evaporator
(8, 8', 8") supply conduit from the evaporator circuit to the column
(9, 9') exchange trays
(10) discharge of distillate
(11) return flow of condensate
(12, 12', 12") discharge of bottom product

The invention claimed is:

1. A distillation column with external circulation evaporator for carrying out a distillation process, in which solid or gel particles or liquid droplets with a higher density than the bottom product are present in the bottom product, in which part of the bottom product is provided for the further treatment and part provided for the evaporator circulation, which parts are withdrawn from the bottom via separate outlets, wherein, in the bottom of the column a sedimentation zone is installed, said sedimentation zone being separated from the rest of the column bottom area by a wall, the lower end of which is open and in hydraulic connection with the column, from whose upper region clarified from solid and/or gel particles the part of the bottom product provided for the evaporator circulation is withdrawn and the part provided for the further treatment outside the column is withdrawn from the lower region of the bottom of the column.

2. A process for the distillation of acrylic acid, wherein the distillation is carried out in the distillation column of claim 1, a raw acrylic acid, comprising acrylic acid oligomers, to be distilled being fed into the column through a feed line, a first bottom product clarified of solid and/or gel particles is withdrawn from the upper part of the sedimentation zone and circulated through the evaporator and back into the column, above the sedimentation zone, a second bottoms product, comprising solid and/or gel particles, is withdrawn from the bottom of the sedimentation zone for further treatment, and a distillate comprising acrylic acid free of said oligomers is withdrawn from the top of the column.

3. The process of claim 2, wherein the evaporator circulation (5') is 20 to 200 $m^3/(h*m^2)$ and the size of the stream (12") withdrawn from the bottom for further treatment is 0.1 to 5 $m^3/(h*m^2)$, each based on the inner cross-sectional area of the column, wherein the ratio of the diameter of the column (1") to the diameter of the sedimentation zone (2") is 1:0.1 to 0.9, and the upwardly directed flow velocity in the sedimentation zone (3") is 0.05 to 1 m/s.

* * * * *